(12) United States Patent
Morris et al.

(10) Patent No.: US 6,347,553 B1
(45) Date of Patent: Feb. 19, 2002

(54) FORCE SENSOR ASSEMBLY FOR AN INFUSION PUMP

(75) Inventors: Matthew Gerald Morris; Donald Frederic Schwartz, both of San Diego, CA (US)

(73) Assignee: Alaris Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/514,532

(22) Filed: Feb. 28, 2000

(51) Int. Cl.[7] .................................................. G01B 7/16
(52) U.S. Cl. .......................................... 73/781; 73/760
(58) Field of Search .......................... 73/763, 768, 774, 73/781, 818, 760

(56) References Cited

U.S. PATENT DOCUMENTS

| | | | | |
|---|---|---|---|---|
| 3,765,497 A | * | 10/1973 | Thordarson | 177/208 |
| 3,975,959 A | * | 8/1976 | Larkin | 73/419 |
| 4,136,554 A | * | 1/1979 | Larson | 73/81 |
| 5,184,107 A | | 2/1993 | Maurer | 338/42 |
| 5,232,449 A | * | 8/1993 | Stern et al. | 604/154 |
| 5,327,785 A | | 7/1994 | Maurer | 73/756 |
| 5,353,003 A | | 10/1994 | Maurer | 338/47 |
| 5,483,994 A | | 1/1996 | Maurer | 138/31 |
| 5,661,245 A | | 8/1997 | Svoboda et al. | 73/726 |
| 5,760,313 A | | 6/1998 | Guentner et al. | 73/862.584 |

* cited by examiner

*Primary Examiner*—Max Noori
(74) *Attorney, Agent, or Firm*—Pennie & Edmonds LLP

(57) ABSTRACT

A force sensor assembly for use in peristaltic pumps includes a housing and a load cell at least partially disposed within the housing. A plunger, pivotable about an axis, has an upper surface and an underside surface distal from the upper surface. The underside surface cooperates with the load cell. The force sensor further includes a mechanism to reduce the load cell's sensitivity to the positioning of an applied force on the upper surface.

24 Claims, 7 Drawing Sheets

FORCE SENSOR ASSEMBLY FOR AN INFUSION PUMP

TECHNICAL FIELD

The present invention relates generally to a force sensor assembly for use in infusion pumps. More particularly, the present invention relates to an assembly that reduces a load cell's sensitivity to the placement of an intravenous tube on the force sensor assembly in an infusion pump.

BACKGROUND OF THE INVENTION

Various devices have been developed to administer intravenous (IV) fluids to patients. One such device, a peristaltic infusion pump, operates a series of fingers or rollers which deform and occlude a resiliently deformable IV drip tube at multiple points sequentially along the tube's length. These occlusions form a wave like motion which forces the IV fluid under positive pressure along the tube. After each successive occlusion, the tube resiliently rebounds to its original diameter. The repetitive deformation of the tube may, however, ultimately weaken the resilience of the tube material. After prolonged use, a tube may not fully rebound to its former shape, thereby partly or fully occluding the tube at a point along its path. In addition, IV drip sets often contain clamps, which can be inadvertently be left closed, thus partly or fully occluding the tube.

In order to effectively control IV fluid delivery, it is essential that the infusion system constantly determine whether fluid is in fact being delivered to the patient. Interruptions of the fluid flow may occur for number of reasons, such as for example, occlusion of the tube or a blocked catheter. If the pump mechanism does not stop when the tube is occluded, either the pump will stall, the pump will continue to run with no fluid delivered, or the fluid pressure in the tube will increase until the obstruction catastrophically clears, possibly injuring the patient.

Accordingly, many infusion pump systems include a force or pressure sensor to determine whether there is an increase or loss of pressure within the tube. The sensor determines whether the fluid flow in the tube has been interrupted, and the pumping mechanism may be stopped and/or medical personnel notified. Because of the potentially harmful consequences of such interruptions, it is important that these sensors be as accurate and reliable as possible. Also, due to an infusion pump's portability and arduous operating conditions, it is desirable for these sensors to be small and rugged.

Force or pressure sensors used in infusion pumps typically contain a plunger that is either constrained in some way, such as with a pin in a hole, or of a free floating type. A constrained plunger type force sensor assembly could be comprised of an actuation plunger connected to a pin positioned and guided within a hole in a sensor housing. A transducer or load cell is positioned along the central axis of the plunger, remote from an IV drip tube. When the IV drip tube is positioned directly over the central axis of the plunger, a force created by the internal pressure of the IV drip tube is applied via the plunger and pin to the load cell, which measures the applied force. In this scenario, the measured force would be comparatively accurate as there is typically only a small loss of transferred force due to friction. However, when the IV drip tube is positioned off-center to the plunger's central axis, the plunger tends to rotate causing side loading on the plunger pin by the sensor housing which may bind the plunger pin in the hole. This side loading creates a friction force between the plunger pin and the sensor housing which results in a loss of force being applied to the load cell. This friction force ultimately leads to inaccurate and unreliable force measurement results. The above scenario may occur for example where an IV tube is misplaced on the force sensor assembly or where the tube drifts along the plunger surface during use.

A free floating plunger type force sensor could be comprised of an actuation plunger positioned within a hole in a sensor housing providing clearance allowing the plunger to float freely. The plunger is positioned over a well of force transmitting gel. The plunger transfers force applied by the IV tubing to the gel, which in turn transfers the force to a transducer or load cell situated within the gel. An example of a gel-type sensor is disclosed in U.S. Pat. No. 5,661,245. The plunger is typically allowed to angulate when a force is applied by the IV tubing to the plunger along an off-center axis. The angled plunger transfers force to the gel with less efficiency, which in turn transfers less force to the transducer or load cell situated within the gel. This reduced force ultimately leads to inaccuracies in the force measurement results. Additional inaccuracies may also be experienced due to frictional reaction forces between the plunger edges and the sensor housing.

Accordingly, there is a need for a small and inexpensive force sensor assembly which provides accurate and reliable results regardless of the placement of the IV tubing on the force sensor assembly.

SUMMARY OF THE INVENTION

According to the invention there is provided a force sensor assembly which is adapted to reduce a load cell's sensitivity to the positioning of an IV tube on the load cell's actuation plunger. The force sensor assembly comprises a housing, a load cell at least partially disposed within the housing and a plunger, which is pivotable about an axis. The plunger may be hinged to the housing or to another fixed point proximate to the housing, and may for example be a living hinge or a small pin pivot hinge. The plunger further comprises an upper surface which may be shaped to compensate for variations in measured force-caused by possible misalignment of the IV tubing on the plunger's upper surface. The plunger also comprises an underside surface distal from the upper surface.

In use an IV tube is placed on the plunger's upper surface, pressure within the IV tube applies a force to the upper surface of the plunger, causing the plunger to pivot about the axis. The pivoting plunger's underside makes contact with the load cell and thereby wholly transfers the applied force to the sensor for measurement.

BRIEF DESCRIPTION OF THE DRAWINGS

For a better understanding of the nature and objects of the invention, reference should be made to the following detailed description taken in conjunction with the accompanying drawings, in which.

Figure 12:
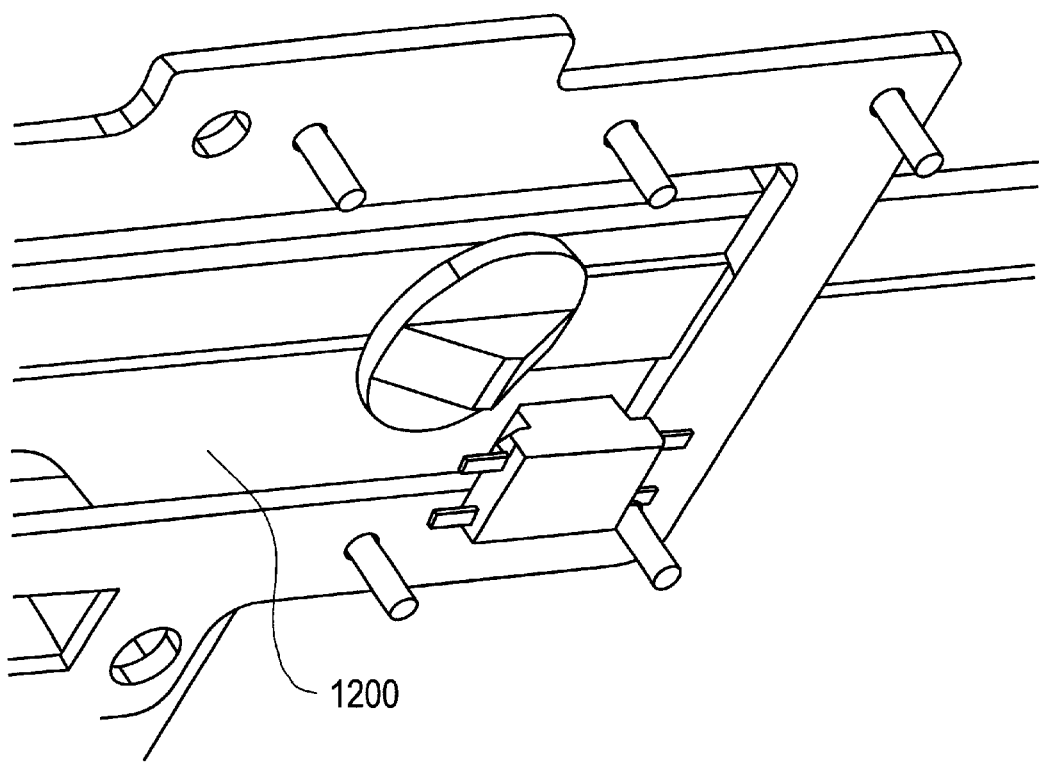

FIG; 11 is an exploded isometric view of a further alternative embodiment of the present invention;

FIG. 12 is an isometric view of yet another alternative embodiment of the present invention.

DETAILED DESCRIPTION OF THE INVENTION

Figure 1:
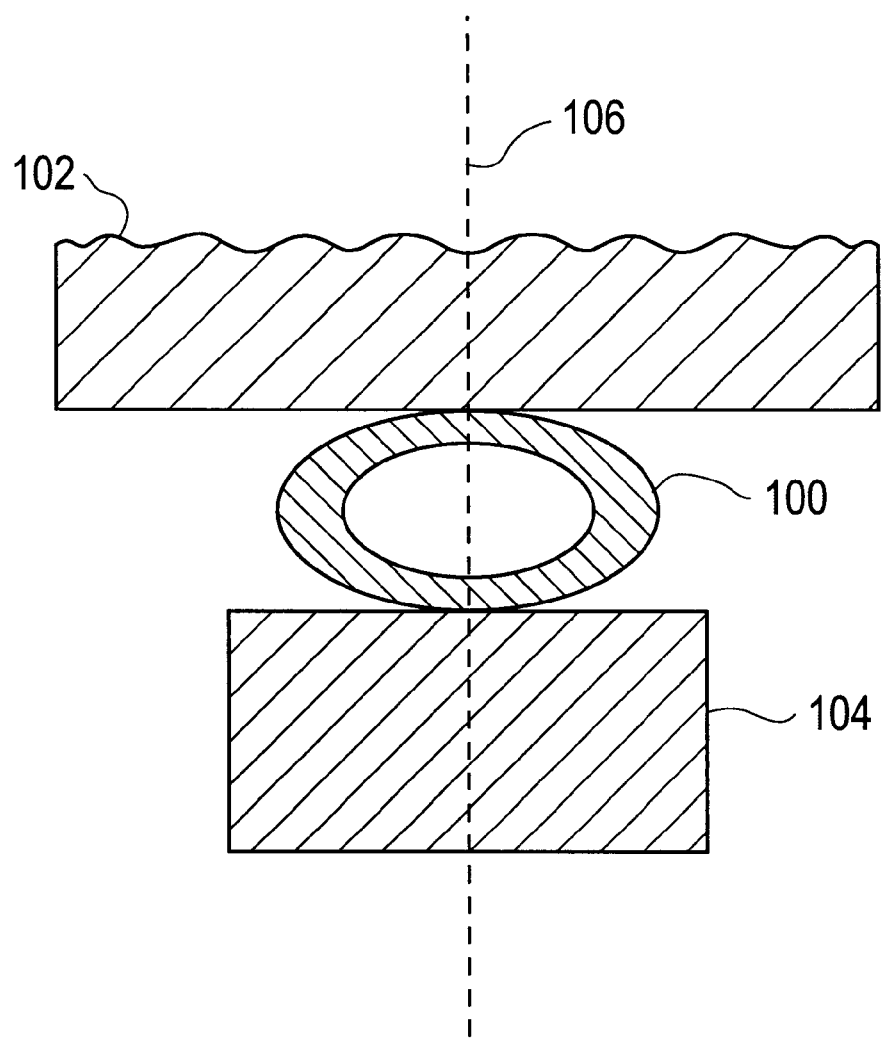
FIG. 1 is a cross sectional diagrammatic view of an IV tube enclosed within an infusion pump.

FIG. 1 illustrates a cross sectional view of an IV tube enclosed within an infusion pump, at the load cell. The IV tube 100 is compressed between a clamping member 102 and a force sensor assembly 104. Ideally the IV tube 100 is positioned directly over the force sensor assembly 104, centered on centerline 106, such that the measured force at the force sensor assembly and a force created by the internal pressure of the IV tube 100 lie along the same plane. While this ideal condition ensures high force measurement accuracy, it is often difficult to guarantee under normal operating conditions.

Figure 2:
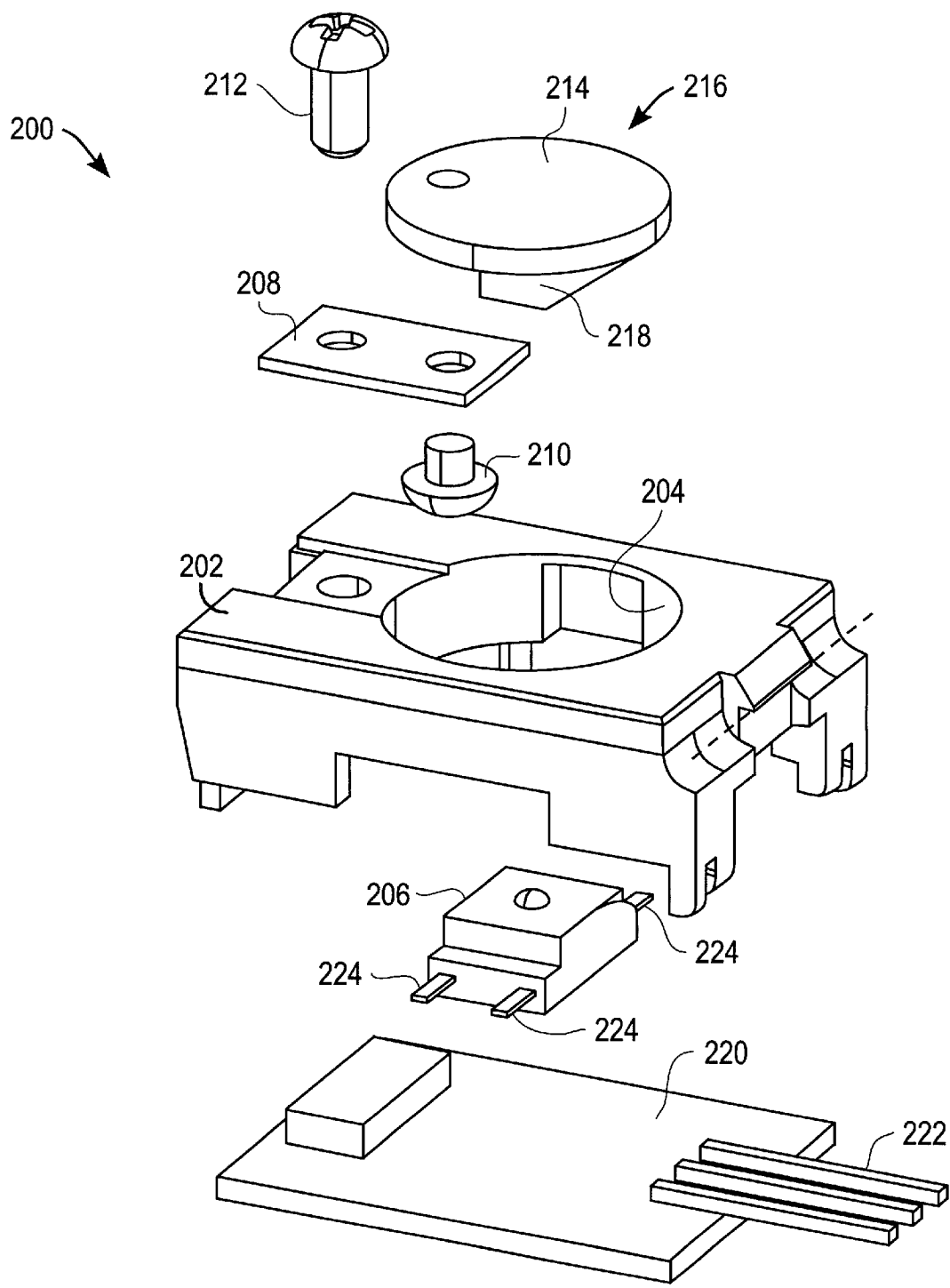
FIG. 2 is an exploded isometric view of an embodiment of the present invention.

FIG. 2 shows an exploded isometric view of an embodiment of the present invention. The sensor assembly 200 comprises a housing structure 202 defining a hole therethrough 204. A pressure or load cell 206 is disposed within the housing 202. The load cell 206 is preferably located directly under the aforementioned hole 204 and is of any typical construction (i.e. gel or oil filled with micromachined silicon die, direct die contact, strain gage etc.). The load cell is selected to have a particular construction that provides little or no mechanical friction in its force transfer mechanism (not shown) to its sensing element (not shown) and is also relatively insensitive to the location of the measured applied force. A suitable sensor may be similar to the sensor disclosed in U.S. Pat. No. 5,760,313 which is hereby incorporated by reference. An actuation plunger 216 is fastened, by means of a screw 210 or the like, to a low mechanical friction hinge 208 that provides support in all directions, but allows rotation in an actuation direction. Such a hinge may, for example, be a living hinge or a small pin pivot hinge as depicted by reference numeral 1102 in FIG. 11. The living hinge may for example be a resilient metal or plastic strip, as is known in the art. Hinge 208 is in turn fastened to the housing 202 by means of another screw 212. It should be appreciated that one could use other fastening means instead of screws 210 and 212, such as for example glue or rivets. Both the shape of the plunger's upper surface 214 and the shape of the plunger's underside 218, may be varied to provide optimum results. This embodiment utilizes a circular shaped upper surface 214 and a chamfered underside 218. The underside 218 of the hinged plunger 216 is shaped so that it preferably contacts with the load cell 206 at a single contact point. Other shapes, such as for example a semicircular shaped underside, may also be utilized. A base 220 seals the housing 202 on the side distal from the hole 204. The base 220 furthermore fastens the sensor 206 in the housing 202 and includes contacts 222 disposed thereon, which connect outputs 224 from the sensor 206 to other measurement circuitry (not shown).

Figure 3:
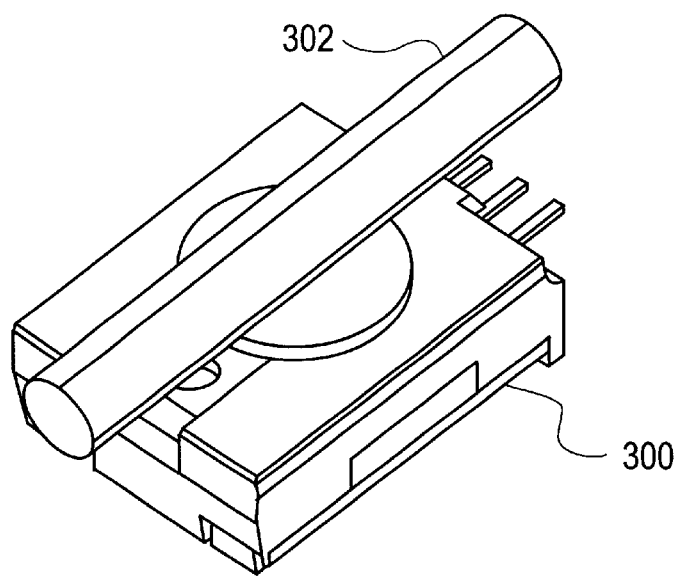
FIG. 3 is an isometric view of the present invention with an IV tube in a first orientation.
Figure 4:
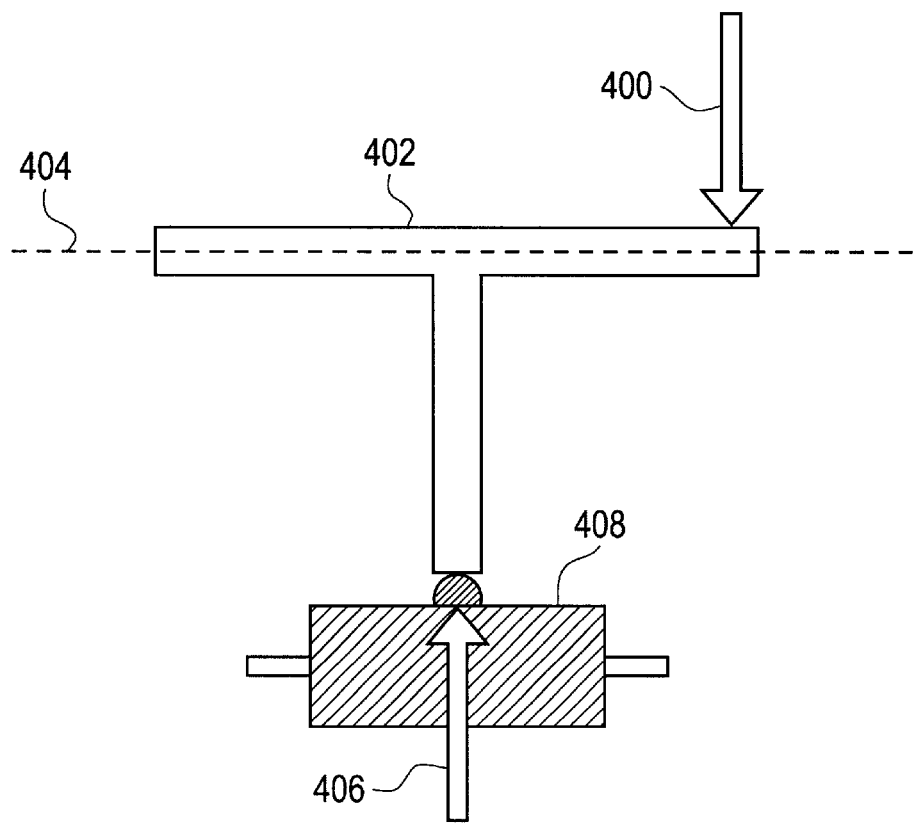
FIG. 4 is a diagrammatic side view of the sensor assembly of FIG. 3.

FIG. 3 shows an isometric view of the present invention with an IV tube in a first orientation. In this preferred embodiment, an IV drip tube 302 is placed across the sensor assembly 300, perpendicular to the hinge axis. This orientation is preferred as the force sensor assembly 300 is not subject to a moment arm effect discussed infra. FIG. 4 illustrates a diagrammatic side view of the sensor assembly of FIG. 3. If the IV tubing crosses the plunger 402 off-center applying a force 400 to the plunger 402, the hinge, rotatable about hinge axis 404, provides a reaction force minimizing or preventing angulation of the plunger 402. This embodiment of the sensor assembly thus gives a more accurate reading irrespective of whether or not the tube is centered above the load cell 408 or not. Therefore, little or no reduction in force is transmitted to the load cell through the plunger from the IV tube if it is positioned off-center to the load cell.

Figure 5:
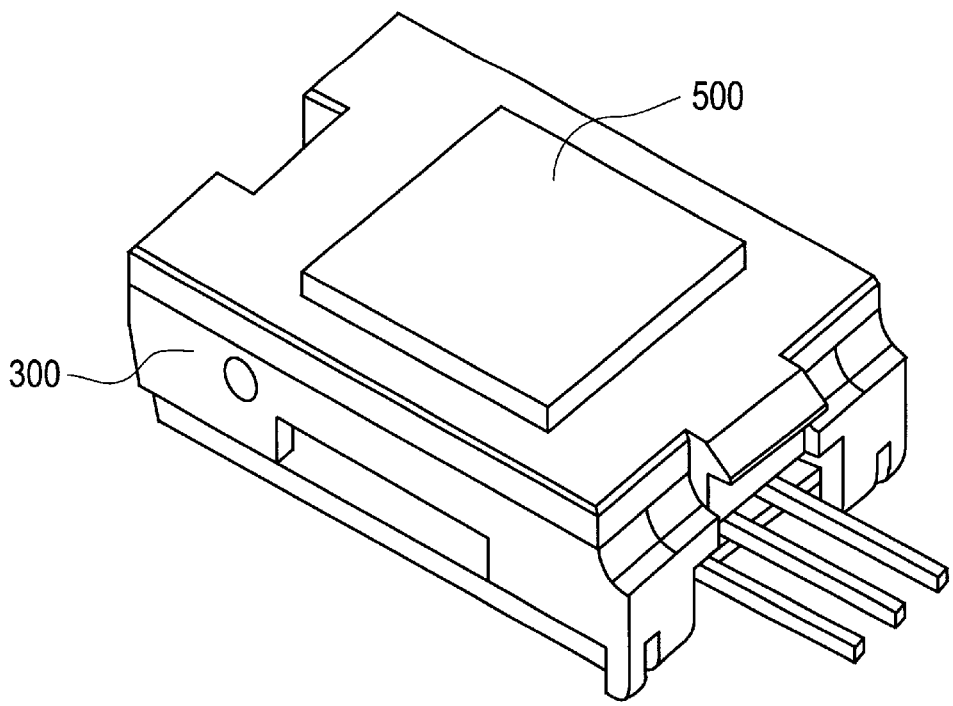
FIG. 5 is an isometric view of an alternative embodiment of the invention.

FIG. 5 shows an isometric view of an embodiment of the invention. Sensor assembly 300 includes a modified upper surface 500 of the plunger. Square upper surface 500 is preferably utilized in conjunction with the embodiment described in relation to FIGS. 3 and 4, where the tube is oriented perpendicular to the hinge axis. The square shaped upper surface 500 maintains a constant area along the hinge axis.

Figure 6:
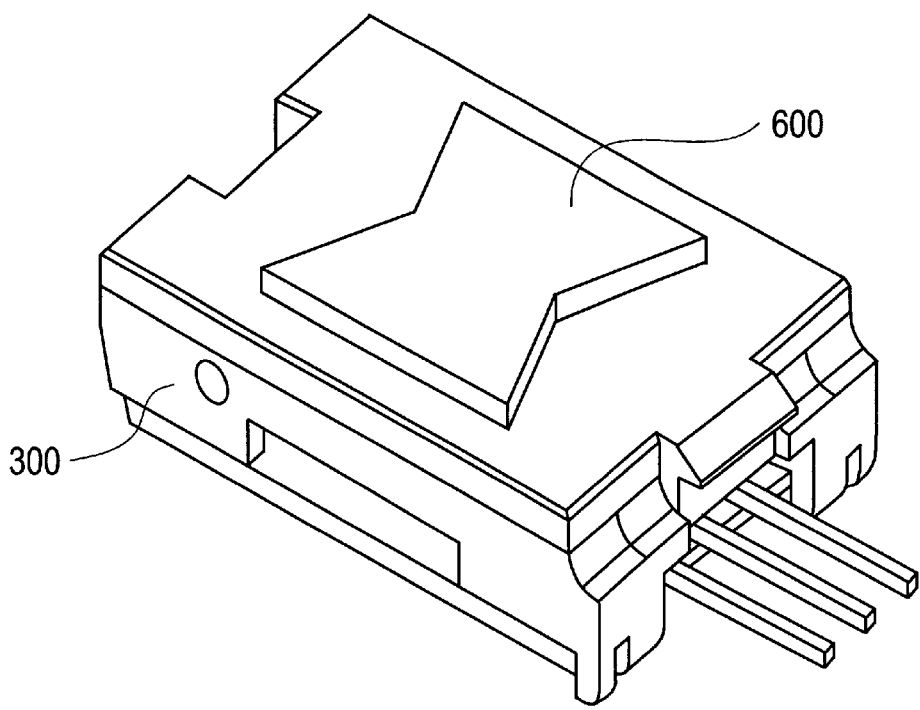
FIG. 6 is an isometric view of yet another alternative embodiment of the invention.

FIG. 6 shows an isometric view of another embodiment of upper surface 600. The upper surface of the plunger may be shaped so that the tubing contact area changes with the distance of the IV tubing from the location of the center of the load cell. A change in the tubing contact area produces a change in the force transmitted to the plunger due to tubing internal pressure, and therefore a change in the force relationship with the load cell. Hourglass shaped upper surface 600 is also preferably utilized in conjunction with the embodiment described in relation to FIGS. 3 and 4. The hourglass shape, when implemented in the appropriate orientation to the hinge axis, can provide an increase in tubing contact area with an increase in the distance from the centerline of the load cell. This can counteract any loss in force to the load cell due to side loading of the hinge components, thus minimizing any effects of the IV tubing being off center.

Figure 7:
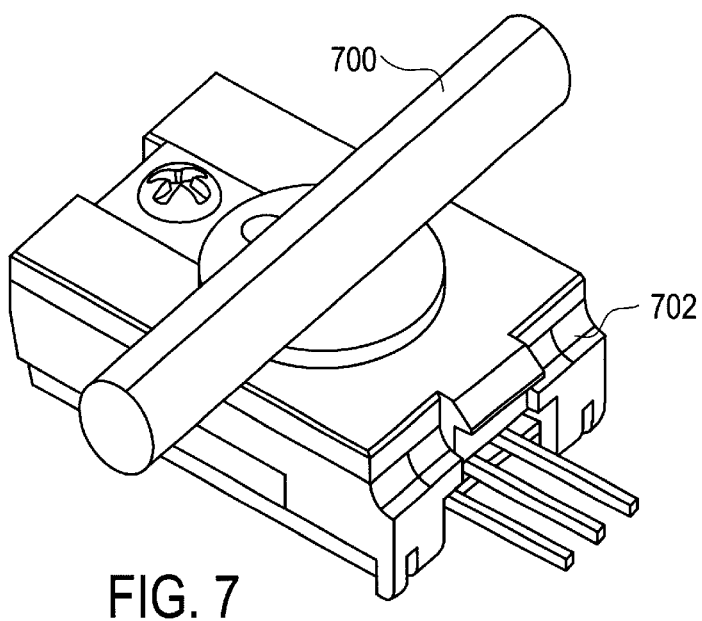
FIG. 7 is an isometric view of an embodiment of the present invention with an IV tube in a second orientation.

FIG. 7 shows an isometric view of an alternative embodiment of the invention with an IV tube in a second orientation. In this embodiment, IV drip tube 700 is placed across the sensor assembly 702, parallel to the hinge axis.

Figure 8:
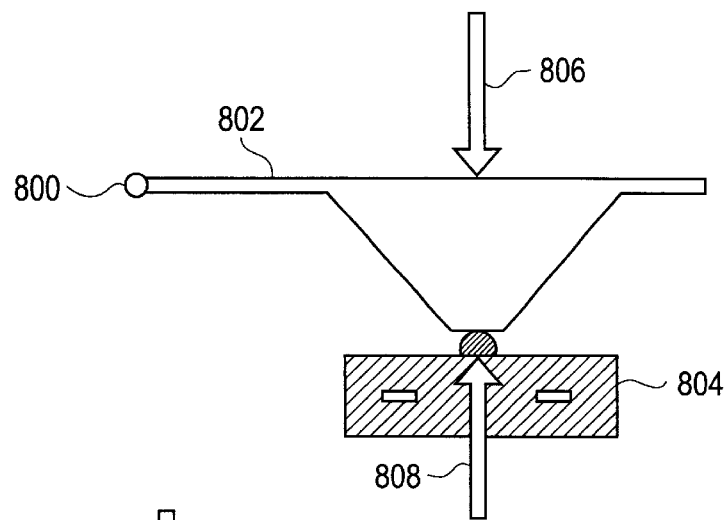
FIG. 8 is a diagrammatic side view of the sensor assembly of FIG. 7.
Figure 9:
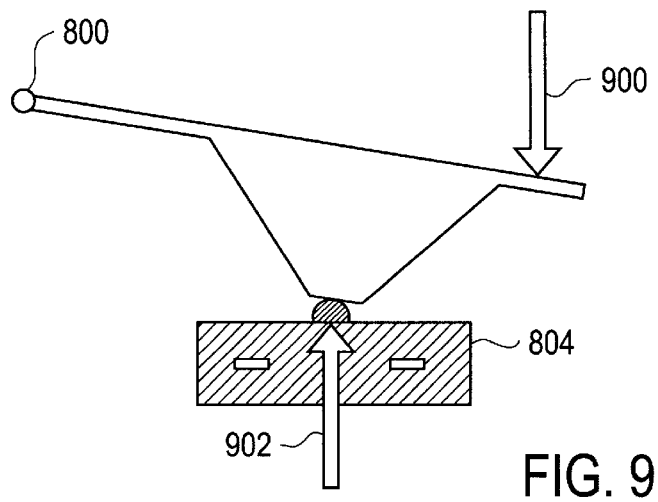
FIG. 9 is a diagrammatic side view similar to that of FIG. 8.
Figure 10:
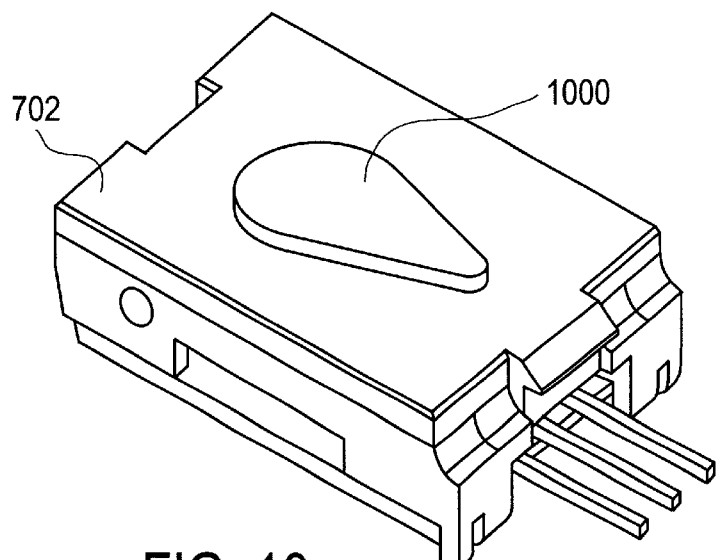
FIG. 10 is an isometric view of an alternative embodiment of the present invention.

FIG. 8 illustrates a diagrammatic side view of the sensor assembly shown in FIG. 7. A plunger 802 is pivotably hinged about a line 800, allowing the plunger to make single point contact with a load cell 804. When a force 806, caused by pressure within the IV tube is applied directly above the load cell 804, the load cell measures a reaction force 808 which is substantially the same as the applied force 806. However, as illustrated in FIG. 9, when a force 900 is applied off-center to the load cell 804, reaction force 902 measured at load cell 804 will be larger than the applied force 900, due to a moment arm effect. As there is no way to accurately determine the distance of the applied force 900 from hinge line 800, this orientation of the IV tube on the sensor assembly is not preferred. To overcome this problem, the shape of the upper surface of the plunger may once again be varied to compensate for the misalignment of the IV tube. Instead of a round upper surface of the plunger as shown in FIGS. 2, 3 and 7, or an hourglass shaped upper surface as shown in FIG. 6, the upper surface of the plunger may be shaped so that the tubing contact area changes with the distance of the IV tubing from the location the hinge axis 800. A change in the tubing contact area produces a change in transmitted force due to the tubing internal pressure and thus a change in the force relationship with the load cell. Variations in measured force caused by the misplacement of the tube on the upper surface of the plunger may therefore be counteracted by tailoring the shape of the upper surface of the plunger. As shown in FIG. 10, a triangular or tear drop shaped upper surface 1000, narrowing away from the hinge axis may preferably be utilized in conjunction with the embodiment described above in relation to FIGS. 7–9, where the tube is oriented parallel to the hinge axis.

Figure 11:
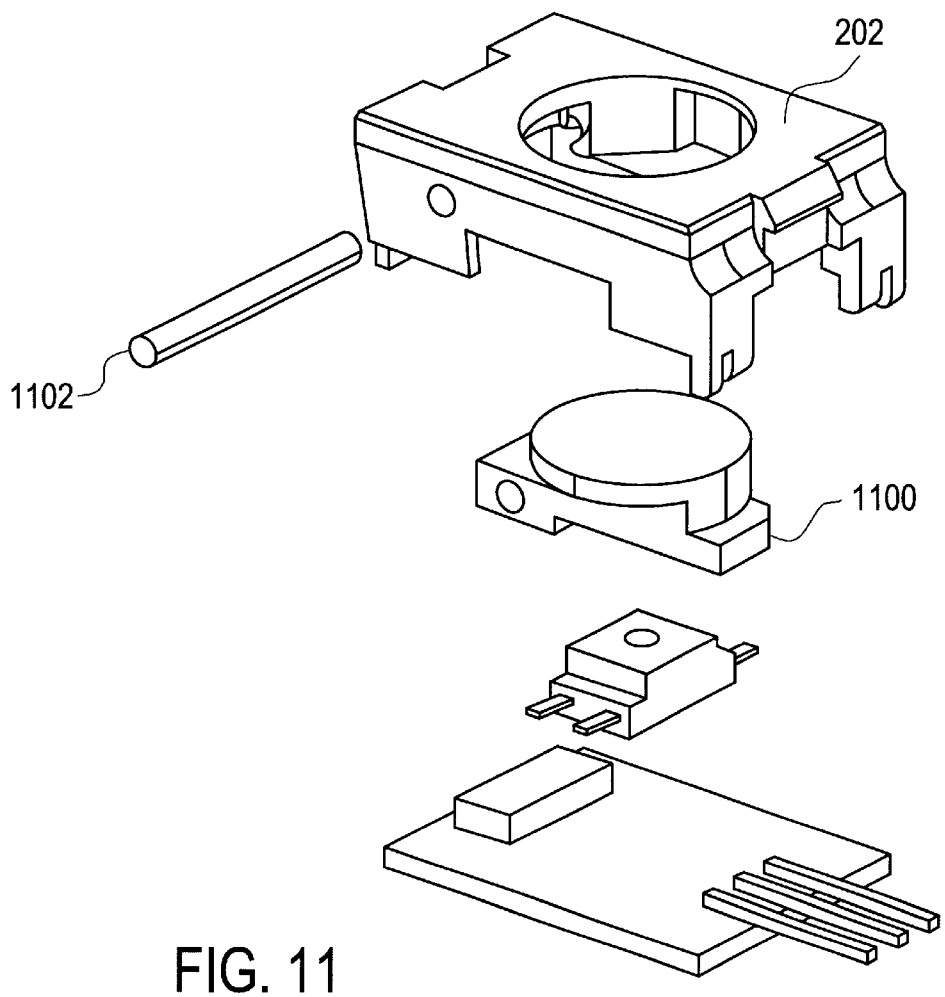

FIG. 11 illustrates an exploded isometric view of another embodiment of the present invention. The living hinge 208 of FIG. 2 has been replaced with a plunger 1100 that is itself hinged to the housing 202 by means of a small hinge pin 1102. The separately hinged actuation plunger 1100 provides stability and low mechanical friction, resulting in low sensitivity to the positioning of an off-centered IV tube.

Other embodiments of the present invention may include a force assembly where the hinge and actuation plunger are formed integral with the hinge support housing (i.e. all molded together as one piece) instead of separate parts. FIG. 12 shows an embodiment of the present invention with a plastic living hinge 1200 integrated into the housing of the IV mechanism. The actuation plunger may also be held by flexible supports at several points around its circumference to minimize moment arm changes with tubing off-center positioning. Furthermore, the hinge could be attached to some other structure of the IV pump proximate to the sensor assembly housing.

The foregoing descriptions of specific embodiments of the present invention are presented for purposes of illustration and description only. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A force sensor assembly for use in peristaltic pumps, comprising:
   a housing;
   a load cell at least partially disposed within said housing;
   a plunger, pivotable about an axis, where said plunger comprises:
      an upper surface; and
      an underside surface distal from said upper surface where said underside surface cooperates with said load cell; and
   a means for reducing said load cell's sensitivity to the positioning of an applied force on said upper surface.

2. A force sensor assembly according to claim 1, wherein said means for reducing said load cell's sensitivity, comprises an upper surface for receiving an intravenous tube perpendicular to said axis.

3. A force sensor assembly according to claim 2, wherein said upper surface is shaped to compensate for variations in measured force caused by the misalignment of said applied force.

4. A force sensor assembly according to claim 3, wherein said upper surface shape is selected from a group consisting of the following shapes:
   circular, square or hourglass.

5. A force sensor assembly according to claim 1, wherein said means for reducing said load cell's sensitivity, comprises an upper surface for receiving an intravenous tube parallel to said axis.

6. A force sensor assembly according to claim 5, wherein said upper surface is shaped to compensate for variations in measured force caused by the misalignment of said applied force.

7. A force sensor assembly according to claim 6, wherein said upper surface shape is selected from a group consisting of the following shapes:
   circular, teardrop or triangular.

8. A force sensor assembly according to claim 1, wherein said plunger further comprises:
   a free end; and
   a pivot end located at said axis.

9. A force sensor assembly according to claim 8, wherein said pivot end is rotatably coupled to said housing.

10. A force sensor assembly according to claim 8, wherein said pivot end is rotatably coupled to a body proximate said housing.

11. A force sensor assembly according to claim 8, wherein said pivot end is rotatably coupled to said housing by means of a hinge.

12. A force sensor assembly according to claim 11, wherein said is hinge is a living hinge.

13. A force sensor assembly according to claim 12, wherein said living hinge is a resilient metal strip.

14. A force sensor assembly according to claim 12, wherein said living hinge is a resilient plastic strip.

15. A force sensor assembly according to claim 11, wherein said hinge is a small pin pivot hinge.

16. A force sensor assembly according to claim 15, wherein said hinge has low mechanical friction.

17. A force sensor assembly according to claim 1, wherein said load cell is a pressure transducer.

18. A force sensor assembly according to claim 1, wherein said load cell has low internal mechanical friction.

19. A force sensor assembly according to claim 1, wherein said load cell itself has a reduced sensitivity to the positioning of the applied force on said upper surface.

20. A force sensor assembly according to claim 1, wherein said underside of said plunger is shaped to contact with said load cell at a single point.

21. A force sensor assembly according to claim 1, wherein said plunger is biased away from said load cell.

22. A force sensor assembly adapted to reduce a load cell's sensitivity to the positioning of an applied force, comprising:
   a housing;
   a load cell at least partially disposed within said housing; and
   a plunger rotatably coupled to said housing by means of a hinge said plunger further comprising:
      an upper surface which is shaped to compensate for variations in measured force caused by the misalignment of said applied force; and
      an underside surface distal from said upper surface,
   such that in use a force applied to said upper surface of said plunger is transferred to said load cell by said underside of said plunger pivoting into contact with said load cell.

23. A force sensor assembly according to claim 22, wherein said hinge is a living hinge.

24. A force sensor assembly according to claim 23, wherein said hinge is a small pin pivot hinge.

* * * * *

EX PARTE REEXAMINATION CERTIFICATE (8622nd)
United States Patent
Morris et al.

(10) Number: US 6,347,553 C1
(45) Certificate Issued: Oct. 11, 2011

(54) FORCE SENSOR ASSEMBLY FOR AN INFUSION PUMP

(75) Inventors: Matthew Gerald Morris, San Diego, CA (US); Donald Frederic Schwartz, San Diego, CA (US)

(73) Assignee: Carefusion 303, Inc., San Diego, CA (US)

Reexamination Request:
No. 90/011,230, Sep. 29, 2010

Reexamination Certificate for:
Patent No.: 6,347,553
Issued: Feb. 19, 2002
Appl. No.: 09/514,532
Filed: Feb. 28, 2000

(51) Int. Cl.
*G01B 7/16* (2006.01)

(52) U.S. Cl. ............................. 73/781; 73/760
(58) Field of Classification Search ............ 73/726
See application file for complete search history.

(56) References Cited

U.S. PATENT DOCUMENTS

| | | |
|---|---|---|
| 3,993,150 A | 11/1976 | Brosh et al. |
| 4,309,993 A | 1/1982 | Brown |
| 4,609,966 A | 9/1986 | Kuisma |
| 4,683,894 A | 8/1987 | Kodama et al. |
| 4,685,336 A | 8/1987 | Lee |
| 4,690,673 A | 9/1987 | Bloomquist |
| 4,784,576 A | 11/1988 | Bloom et al. |
| 4,784,577 A | 11/1988 | Ritson et al. |
| 4,840,542 A | 6/1989 | Abbott |
| 5,217,355 A | 6/1993 | Hyman et al. |
| 5,335,551 A | 8/1994 | Ohnishi et al. |
| 5,533,981 A | 7/1996 | Mandro et al. |
| 5,549,460 A | 8/1996 | O'Leary |
| 5,551,850 A | 9/1996 | Williamson et al. |
| 5,630,710 A | 5/1997 | Tune et al. |
| 5,658,133 A | 8/1997 | Anderson et al. |
| 5,661,245 A | 8/1997 | Svoboda et al. |
| 5,760,313 A | 6/1998 | Guentner et al. |
| 5,782,805 A | 7/1998 | Meinzer et al. |
| 5,840,058 A | 11/1998 | Ammann et al. |
| 5,842,841 A | 12/1998 | Danby et al. |

FOREIGN PATENT DOCUMENTS

| | | |
|---|---|---|
| DE | 3838689 | 6/1990 |
| EP | 0132047 | 1/1985 |
| JP | 04346044 | 12/1992 |
| WO | WO91/16609 | 10/1991 |
| WO | WO98/36254 | 8/1998 |

OTHER PUBLICATIONS

Bonenberger, Paul R. The First Snap–Fit Handbook: Creating Attachments for Platic Parts. Hanser Gardner Publications, Inc. 2000.
Handbook of Plastics Joining: A Practical Guide. 1997.
Smith, Stuart T. Flexures: Elements of Elastic Mechanisms. Gordon and Breach Science Publishers, 2000.
Timoshenko, S.P. and J.M. Gere. Mechanics of Materials. Van Nostrand Reinhold Co., 1972.
Ronald D. Beck, How to Fasten and Join Plastics, Materials Engineering, Mar. 1971, pp. 32–36 and 66–68, vol. 73, No. 3 (Reinhold Publishing Corporation), U.S.
Ronald D. Beck, Plastic Product Design, 1970, pp. v–vi (preface) and 239–286 (Van Nostrant Reinhold Co.), U.S.
Ronald D. Beck, Plastic Product Design (Second Edition), 1980, pp. iii (preface) and 200–246 (Van Nostrand Reinhold Co.), U.S.
Paul D. Q. Campbell, Plastic Component Design, 1996, pp. 1–3 and 59–93 (Industrial Press, Inc.), U.S.
Expert Report of Peter Crosby (on invalidity), *CareFusion 303, Inc. v. Sigma International*, USDC SDCA, Case No. 10–CV–0442 DMS (Wmc), Jun. 2011.

*Primary Examiner* — Robert Nasser

(57) ABSTRACT

A force sensor assembly for use in peristaltic pumps includes a housing and a load cell at least partially disposed within the housing. A plunger, pivotable about an axis, has an upper surface and an underside surface distal from the upper surface. The underside surface cooperates with the load cell. The force sensor further includes a mechanism to reduce the load cell's sensitivity to the positioning of an applied force on the upper surface.

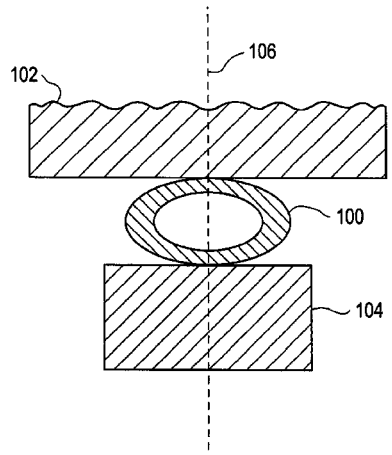

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-23 is confirmed.

Claim 24 is determined to be patentable as amended.

New claims 25-29 are added and determined to be patentable.

24. A force sensor assembly according to claim [23] *22*, wherein said hinge is a small pin pivot hinge.

*25. The force sensor assembly according to claim 1, wherein the means for reducing the load cell's sensitivity to the positioning of an applied force on said upper surface comprises flexible supports around a circumference of the plunger.*

*26. The force sensor assembly according to claim 1, wherein the means for reducing said load cell's sensitivity to the positioning of an applied force on said upper surface comprises a shaped upper surface that has a constant contact area along the axis of rotation.*

*27. The force sensor assembly according to claim 1, wherein said underside surface contacts said load cell when said plunger is in a pivoted position.*

*28. A force sensor assembly for use in peristaltic pumps, comprising:*
  *a housing;*
  *a load cell at least partially disposed within said housing;*
  *a plunger, pivotable about an axis, where said plunger comprises:*
    *a shaped upper surface that has a constant contact area along the axis of rotation; and*
    *an underside surface distal from said upper surface where said underside surface cooperates with said load cell; and*
  *flexible supports for reducing said load cell's sensitivity to the positioning of an applied force on said upper surface.*

*29. The force sensor assembly according to claim 28, wherein said underside surface contacts said load cell when said plunger is in a pivoted position.*

\* \* \* \* \*

(12) EX PARTE REEXAMINATION CERTIFICATE (9430th)
United States Patent
Morris et al.

(10) Number: US 6,347,553 C2
(45) Certificate Issued: Nov. 30, 2012

(54) FORCE SENSOR ASSEMBLY FOR AN INFUSION PUMP

(75) Inventors: Matthew Gerald Morris, San Diego, CA (US); Donald Frederic Schwartz, San Diego, CA (US)

(73) Assignee: Carefusion 303, Inc., San Diego, CA (US)

Reexamination Request:
No. 90/012,141, Feb. 15, 2012

Reexamination Certificate for:
Patent No.: 6,347,553
Issued: Feb. 19, 2002
Appl. No.: 09/514,532
Filed: Feb. 28, 2000

Reexamination Certificate C1 6,347,553 issued Oct. 11, 2011

(51) Int. Cl.
*G01B 7/16* (2006.01)

(52) U.S. Cl. .......................................... 73/781; 73/760
(58) Field of Classification Search ....................... None
See application file for complete search history.

(56) References Cited

To view the complete listing of prior art documents cited during the proceeding for Reexamination Control Number 90/012,141, please refer to the USPTO's public Patent Application Information Retrieval (PAIR) system under the Display References tab.

*Primary Examiner* — Kenneth J Whittington

(57) ABSTRACT

A force sensor assembly for use in peristaltic pumps includes a housing and a load cell at least partially disposed within the housing. A plunger, pivotable about an axis, has an upper surface and an underside surface distal from the upper surface. The underside surface cooperates with the load cell. The force sensor further includes a mechanism to reduce the load cell's sensitivity to the positioning of an applied force on the upper surface.

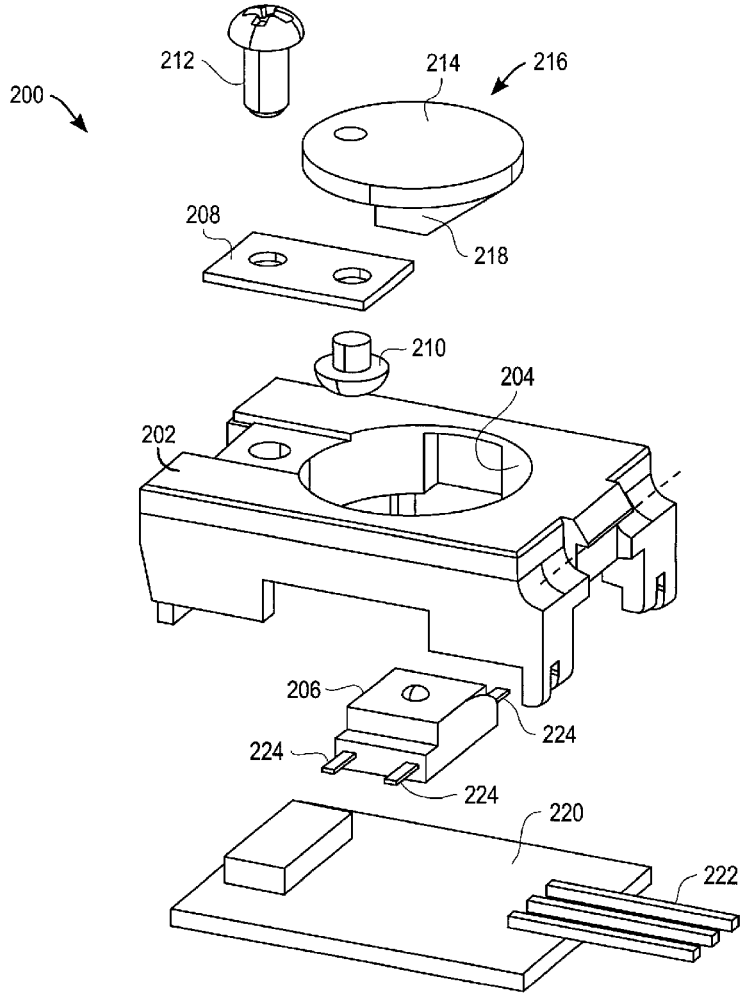

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

New claim 30 is added and determined to be patentable.

Claims 2-29 were not reexamined.

*30. A force sensor assembly for use in peristaltic pumps, comprising:*
*a housing;*
*a load cell at least partially disposed within said housing;*
*a plunger, pivotable about an axis, where said plunger comprises:*
*an upper surface; and*
*an underside surface distal from said upper surface where said underside surface cooperates with said load cell; and*
*a means for reducing said load cell's sensitivity to the positioning of an applied force on said upper surface, wherein a direction of the applied force on said upper surface is in an opposite direction from a reaction force applied by said load cell to said underside surface.*

\* \* \* \* \*